United States Patent [19]

Buhl et al.

[11] Patent Number: 5,776,563
[45] Date of Patent: Jul. 7, 1998

[54] DRIED CHEMICAL COMPOSITIONS

[75] Inventors: Steven N. Buhl, Cupertino; Bhaskar Bhayani, Fremont; Chi-Sou Yu, Saratoga; Thuy N. Tang, San Jose, all of Calif.

[73] Assignee: Abaxis, Inc., Sunnyvale, Calif.

[21] Appl. No.: 466,155

[22] Filed: Jun. 6, 1995

Related U.S. Application Data

[63] Continuation of Ser. No. 134,574, Oct. 8, 1993, abandoned, which is a continuation-in-part of Ser. No. 747,179, Aug. 19, 1991, Pat. No. 5,413,732.

[51] Int. Cl.$^6$ .................................................. B65D 79/00
[52] U.S. Cl. ......................................... 428/34.1; 206/527
[58] Field of Search ............................ 206/527; 428/34.1

[56] References Cited

U.S. PATENT DOCUMENTS

| | | | |
|---|---|---|---|
| 3,721,725 | 3/1973 | Briggs | 264/6 |
| 3,819,488 | 6/1974 | Rush | 195/103.5 |
| 3,928,566 | 12/1975 | Briggs et al. | 424/94.3 |
| 3,932,943 | 1/1976 | Briggs | 34/5 |
| 4,115,537 | 9/1978 | Driscoll | 424/1 |
| 4,295,280 | 10/1981 | Krupey | 34/5 |
| 4,351,158 | 9/1982 | Hurwitz | 62/60 |
| 4,588,696 | 5/1986 | Eskelson | 436/130 |
| 4,678,812 | 7/1987 | Bollin, Jr. | 514/777 |
| 4,712,310 | 12/1987 | Roy | 34/5 |
| 4,716,119 | 12/1987 | Rehner | 436/16 |
| 4,755,461 | 7/1988 | Lawson | 435/13 |
| 4,762,857 | 8/1988 | Bollin, Jr | 514/777 |
| 4,820,627 | 4/1989 | McGeehan | 435/4 |
| 4,848,094 | 7/1989 | Davis | 62/64 |
| 4,859,606 | 8/1989 | Cram et al. | 436/79 |
| 5,061,381 | 10/1991 | Burd | 210/789 |
| 5,122,284 | 6/1992 | Braynin | 210/782 |
| 5,275,016 | 1/1994 | Chatterjee | 62/381 |

OTHER PUBLICATIONS

Driscol, et al., Clin. Chem. (1983) 29:1609–1615.

*Primary Examiner*—D. S. Nakarani
*Attorney, Agent, or Firm*—Townsend and Townsend and Crew

[57] ABSTRACT

The present invention provides dried chemical compositions comprising dried beads. Typically, the beads comprise reagents suitable for analysis of biological samples, in particular analysis of blood samples in centrifugal analyzers.

4 Claims, No Drawings

DRIED CHEMICAL COMPOSITIONS

The present application is a continuation of application U.S. Ser. No. 08/134,574 filed Oct. 8, 1993, abandoned, which is a continuation in part of application U.S. Ser. No. 07/747,179; filed Aug. 19 1991, now U.S. Pat. No. 5,413,732, which is incorporated herein by reference.

BACKGROUND OF THE INVENTION

1. Field of Invention

This invention relates to novel compositions comprising dried chemical compounds and to methods for their preparation. In particular, it relates to novel dried beads useful in a number of applications such as preparation of pharmaceutical compositions or analytical reagents.

In preparing chemical compounds for various uses such as convenient and efficient testing of clinical biological samples, it is frequently important to obtain dry chemical blends in uniform, discrete amounts. These compositions must be efficiently and economically prepared in small precisely measured quantities. Chemical compositions comprising organic materials, however, tend to spoil or degrade on storage, thus creating quality control problems. Thus, various chemical compositions are typically provided in dried form to increase stability. Current technology for producing dry chemical blends involves procedures such as dry blending, spray drying, or fluid bed drying. All three of these procedures, however, have limitations that make them costly, inefficient or difficult to carry out.

In dry blending technology, it is difficult to obtain homogeneous blends of chemicals that have different densities. Moreover, homogeneity is particularly difficult to achieve when very small amounts of ingredients are mixed with large amounts of others. Once made homogeneous, it is extremely difficult to reproducibly (within 1 percent) dispense small amounts (less than about 10 mg) of the blended chemicals.

Spray drying technology provides more homogenous blends of chemicals because the reagents are first dissolved in liquid. Using spray drying, however, it is difficult and costly to obtain precisely sized amounts of blended chemicals. As generally practiced, this process yields particles with size distributions having coefficients of variation greater than 20 percent. The resulting particles have to be reprocessed (usually agglomerated) to obtain uniform particle sizes. After agglomeration, the particles are generally less soluble than the original spray dried particles. Moreover, these procedures typically use fluorocarbon cryogenic solutions which are hazardous to the environment.

Fluid bed technology relies upon spraying a liquid reagent blend onto a particle and drying the liquid to obtain a particle coated with the blended reagents. Using this procedure, it is difficult to obtain uniformly sized particles and to produce a uniform coating.

Of particular interest to the present invention are reagents useful in analyzing biological samples, such as blood plasma or serum, in centrifugal analyzers. The rotors used in such analyzers measure volumes of the sample to be tested, mix the sample with an appropriate diluent and separate fluid from cellular components. The rotors also provide a plurality of separate test wells containing chemical reagents in which discrete volumes are optically tested.

Analysis of biological samples in the test wells of centrifugal rotors impose a number of requirements on the reagents used for analysis. In particular, because the analysis is typically highly automated, speed of analysis is at a premium. In addition, many clinical diagnostic analyses require that measurements be made within a short time after the sample is added to the reagent. Thus, the dried reagent preparations must dissolve quickly in the sample solution. In addition, rapid rehydration of the reagents can cause bubble formation, which adversely affects results by interfering with optical measurement.

The prior art thus lacks dried chemical compositions which avoid the above problems. In addition, the prior art lacks economical and reliable dried chemical which dissolve quickly in sample solutions. The present application addresses these and related problems.

2. Description of Background Art

U.S. Pat. Nos. 3,721,725 and 3,932,943 relate to methods for producing lyophilized reagents comprising spraying a solution containing the reagents into a moving bath of fluorocarbon refrigerants and lyophilizing the resultant frozen droplets. U.S. Pat. No. 4,848,094 discloses methods for the generation of essentially spherical frozen droplets and improved methods for removing frozen droplets from a cryogenic liquid. U.S. Pat. No. 4,655,047 describes methods for freezing drops of relatively thick liquids by dropping them from a small height into a cryogenic material. U.S. Pat. No. 3,819,488 provides stable lyophilized diagnostic compositions for determining glutamic oxalic transaminase and glutamic pyruvic transaminase activities. U.S. Pat. No. 4,588,696 relates to preparation of tablets used in testing for formaldehyde and/or glutaraldehyde. U.S. Pat. Nos. 4,295,280, 4,351,158, and 4,712,310 all relate to methods for preparing homogenous preparations comprising compounds which are incompatible. U.S. Pat. No. 4,820,627 discloses a fluidized bed process for preparing particles suitable for tableting into diagnostic reagents. U.S. Pat. No. 4,115,537 relates to diagnostic tablets containing ion exchange resins. U.S. Pat. No. 4,755,461 is directed to tableted blood plasma compositions. U.S. Pat. Nos. 4,678,812 and 4,762,857 both relate to diagnostic tablets comprising trehalose as an excipient and stabilizer. The use of TRITONO® X-100 is also disclosed. U.S. Pat. No. 4,716,119 discloses the addition of tetramethylammonium acetate to blood serum. Romanian Patent Appln. No. 85,155 relates to enzymatic alkaline phosphatase reagent tablets comprising p-nitrophenyl phosphate. Driscoll et al., *Clin. Chem.*, 29:1609–1615 (1983) discloses an instrument/reagent system comprising tableted reagents for performing photometric assays.

SUMMARY OF THE INVENTION

The present invention provides methods for forming dried chemical compositions. The method comprise forming a solution comprising a desired compound, dispensing uniform, precisely measured drops of the solution into a cryogenic liquid, preferably unagitated liquid nitrogen, and drying the frozen drops to form dried beads comprising the compound.

The step of drying is preferably accomplished by lyophilizing the frozen drops for about 4 hours to about 24 hours at about 50 to about 450 mTorr.

A variety of solutions and compounds can be used in the methods. Typically, the solution is an aqueous solution and the compound is a reagent for the analysis of a biological sample. Exemplary compounds include sodium fluoride and potassium oxalate.

The dried beads produced by the methods typically have a mean diameter between about 1.5 mm and about 5 mm and are uniform in size and weight. The coefficient of weight variation of the beads is preferably less than about 3.0%. The uniform, precisely measured drops used to form the beads typically have a volume between about 1.5 µl and about 25 µl. To increase uniformity, the aqueous solution can be degassed before dispensing the drops.

The beads typically comprise fillers in a concentration sufficient to facilitate formation of a chemical lattice in the beads. Preferred fillers include polyethylene glycol, myo-inositol, polyvinylpyrrolidone, dextran, sodium cholate, mannitol, bovine serum albumin, trehalose, or a combination thereof.

The beads may also comprise a surfactants at a concentration sufficient to inhibit bubble formation when the dried beads dissolve. Exemplary surfactants include octoxynol 9 or polyoxyethlene 9 lauryl ether.

DETAILED DESCRIPTION OF THE PREFERRED EMBODIMENTS

The present invention provides dried chemical composition, typically in the form of beads. The compositions can be used in any application in which stable, dried chemical compositions are required. Because the compositions are dry and free-flowing, they may be used to provide precisely measured quantities of particular compositions. In addition, the compositions are typically in the form of a dried homogenous, mixture of components in a precise ratio. Thus, the problems of accurately dispensing dry mixtures is avoided using the compositions of the invention.

The compositions can comprise essentially any compound which can be prepared in a liquid solution, dispensed as drops into a cryogenic liquid and dried. For instance, the compositions may comprise therapeutically active compounds for use in pharmaceutical compositions. Various biological materials can also be included in the compositions. In addition, the compositions can comprise reagents for analysis of various samples such as biological, chemical, soil samples and the like. In one embodiment they are used in centrifugal rotors and analyzers which allow rapid and economical analysis of blood samples.

In some embodiments, the dried compositions are provided in the form of beads or spheres that comprise a chemical lattice to facilitate rapid and complete dissolution of the spheres in an aqueous solution. They also comprise a surfactant at a concentration sufficient to inhibit bubble formation as the spheres dissolve. The beads may be used in combination with diluent solutions comprising isotonic concentrations of compounds having substantially no effect on the assays.

The dried compositions of the invention are particularly useful in the preparation of pharmaceutical compositions comprising any of a number of therapeutically active compounds, such as analgesics, steroidal and non-steroidal anti-inflammatory compounds, immunosuppressants, chemotherapeutic agents, antibiotics, vitamins and other nutritional additives (e.g., trace elements and amino acids), plasma fractions (e.g., Factor IX) and hormones.

Methods and compounds for preparing administrable compositions will be known or apparent to those skilled in the art and are described in more detail in for example, *Remington's Pharmaceutical Science*, 17th ed., Mack Publishing Company, Easton, Pa. (1985), which is incorporated herein by reference.

The compositions of the invention are prepared as formulations comprising pharmaceutically acceptable media, for example, saline, phosphate buffered saline (PBS), Ringer's solution, dextrose/saline, Hank's solution, and glucose.

The compositions may contain pharmaceutically acceptable auxiliary substances as required to approximate physiological conditions, such as buffering agents, tonicity adjusting agents, wetting agents, detergents, and the like. Additives may also include additional active ingredients, e.g., bactericidal agents, or stabilizers.

The pharmaceutical compositions can be prepared for transdermal or parenteral administration, e.g., intravenously, subcutaneously, or intramuscularly. Orally administratable forms may also be desired and can be provided by modifying the composition to bypass the stomach environment. The composition can be used for prophylactic and/or therapeutic treatment. Typically, the compositions comprise the therapeutically active compound dissolved or suspended in an acceptable carrier, preferably an aqueous carrier. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The concentration of the therapeutically active compound will vary widely, depending upon the compound being administered, the form of administration, the condition being treated and the like. The concentration will also depend upon desired fluid volumes, viscosities, etc., in accordance with the particular mode of administration selected.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, glycol and the like. For oral administration, a pharmaceutically acceptable nontoxic composition is formed by incorporating any of the normally employed excipients, such as those carriers previously listed, and generally 10–95% of active ingredient.

The compositions of the invention are also useful in preservation of biological materials in dried form. For instance, the dried beads of the invention may comprise biological samples such as blood or plasma, urine, tissue samples, various proteins (e.g., blood factors, immunoglobulins, enzymes and the like) spinal fluid, sputum, genetic material (DNA or RNA) or other samples suitable for analysis or other uses.

The compositions are also suitable for providing precisely measured aliquots of compounds to be mixed with a sample to preserve the sample or otherwise keep it in a condition suitable for later analysis. For instance, the beads of the invention may comprise anticoagulants (e.g., potassium oxalate, lithium heparin) or metabolic inhibitors (e.g., sodium fluoride) for use in blood collection tubes.

The dried beads of the invention can also comprise reagents used in the analysis of a wide variety of compositions. Examples include the analysis of soil samples, industrial chemicals, food chemicals, agricultural chemicals and the like. In one embodiment, the beads and diluents of the present invention are used in centrifugal analyzers for optically analyzing biological fluids, in particular blood plasma or serum. Centrifugal rotors used in such analyzers typically comprise means for mixing the blood with an appropriate diluent and separating plasma from cellular material. The rotors also provide for distribution of the diluted plasma into a plurality of cuvettes within the rotor so that different optical analytic procedures may be performed without having to transfer aliquots of the fluid from the apparatus. One or more reagent beads comprising the reagents necessary for a desired assay are provided in each cuvette.

The rotors and methods described in the following U.S. Patents are preferably used: U.S. Pat. Nos. 5,061,381, 5,173,193, 5,186,844, and 5,122,284. The entire disclosure of these patents are incorporated herein by reference. The above applications disclose centrifugal rotors for separating plasma from whole blood that include a plurality of internal chambers and passages for combining blood plasma or serum with one or more reagents and distributing the plasma or serum to a plurality of individual test wells. The chambers and passages necessary for separating the whole blood into plasma are located radially outward from metering chambers that deliver precisely measured volumes of blood and/or diluent to a separation chamber. The separation chamber includes a radially-outward cell trap. Spinning of the rotor causes the cellular components of the whole blood to be sequestered in the cell trap. The separated plasma is then delivered to a plurality of test wells or cuvettes. The above separation and aliquoting steps typically occur as a result of centrifugal force generated by the spinning rotor.

The compositions of the present invention in combination with the rotors described above are particularly suitable for analyzing blood plasma or diluted blood plasma. They are also useful with a wide variety of other biological fluids, such as urine, sputum, semen, saliva, ocular lens fluid, cerebral fluid, spinal fluid, amniotic fluid, and tissue culture media, as well as food and industrial chemicals, and the like.

The compositions of the present invention are particularly suitable for performing a wide variety of analytic procedures which are beneficially or necessarily performed on chemical, soil or biological samples, such as blood plasma or diluted plasma. The analytic procedures will generally require that the sample be combined with one or more reagents so that some detectable change occurs in the sample which may be related to measurement of a particular component or characteristic of the sample. For instance, the sample may undergo a optically detectable reaction or other change which results in a change in color, fluorescence, luminescence, or the like, which may be measured by conventional spectrophotometers, fluorometers, light detectors, etc.

In some cases, immunoassays and other specific binding assays may be performed. In these embodiments, the compositions of the invention will comprise antibodies, or fragments thereof, which are used to detect the presence of an antigen in the sample.

Generally, the procedures must be homogeneous and do not require a separation step. In other cases, it will be possible to accommodate heterogeneous assay systems by providing a means to separate blood plasma, a precipitate, or bound material from the test wells after an immunological reaction step has occurred.

If blood is used as the biological sample, conventional blood assays can be performed such as glucose, lactate dehydrogenase, serum glutamic-oxaloacetic transaminase (SGOT), serum glutamic-pyruvic transaminase (SGPT), blood urea (nitrogen) (BUN), total protein, alkalinity, alkaline phosphatase, c-reactive protein, bilirubin, calcium, chloride, sodium, potassium, magnesium, and the like. This list is not exhaustive and is intended merely as being exemplary of the assays which may be performed using the apparatus and method of the present invention. Usually, these tests will require that the blood plasma be combined with one or more reagents which result in a visually detectable, usually photometrically detectable, change in the plasma.

To prepare the compositions of the invention, a solution, typically an aqueous solution, comprising the chemicals to be dried is prepared. To ensure uniform composition of the dried beads, the solution must be homogeneous and all constituents must be fully dissolved or in suspension. Individual drops of the solution are then dispensed into a cryogenic liquid, preferably liquid nitrogen. A cryogenic liquid as used herein refers to a liquified gas having a normal boiling point below about −75° C., preferably below about −150° C.

The frozen masses are then dried, typically lyophilized, to produce the dried beads. The beads typically comprise less than about 6% residual moisture, preferably less than about 3%. Lyophilization or drying step is not a critical aspect of the invention and can be carried out according to any of a number of standard procedures known in the art. Typically, the frozen drops are lyophilized for about 4 hours to about 24 hours at about 50 to about 450 mTorr, preferably, about 6 hours at about 200 mTorr.

The drops are uniform and precisely measured so that the resulting dried beads have uniform mass. When the drops are uniform and precisely measured, the imprecision of the mass (coefficient of weight variation) of the beads prepared from the drops is less than about 3%, and preferably between about 0.3% and about 2.5%. To further decrease the coefficient of weight variation, the aqueous solution is preferably degassed using a vacuum pump or vacuum line before the drops of solution are dispensed.

To obtain values for coefficient of weight variation, known quantities of beads are weighed. The coefficient of variation (C.V.) is then determined as follows:

$$C.V. = J\sqrt{x} \times 100$$

wherein $$J = \text{standard deviation (for } n \text{ bead)} = \left[ \frac{(x - \bar{x})^2}{n - 1} \right]^{1/2}$$

x=weight of one bead x̄=mean (for "n" bead)=Σx/n

The uniformity of the beads produced by this method obviates the need for an additional tableting step to obtain uniform size. The drops can be dispensed by any of a number of means which provide the necessary precision. Typically, an IVEK model AAA pump (N. Springfield, Vt.) is used. The solution is usually dispensed in discrete drops having a volume between about 1.5 μl and about 25 μl, preferably between about 2.5 μl and about 10 μgl. The exact volume of the drops will depend upon the particular application. For instance, in preparing reagent beads for total protein determinations, 2.96 μl drops are typically used, for C-reactive protein and alkaline phosphatase determinations, 2.67 μl are used. Volumes appropriate for other tests are as follows: SGOT, 4.0 μl; potassium, 4.0 μl; creatinine, 4.0 ml; bilirubin, 2.667 μl; amylase, 2.667 μl; cholesterol, 2.667 μl; uric acid, 3.478 μl; and glucose, 2.065 μl.

As noted above, the methods of the invention can be used to make chemical beads for aliquoting a variety of chemicals. For example, volumes appropriate for food and agricultural chemicals include lactic acid, 4.0 μl and citric acid 2.065 μl. In the case of the anticoagulant and metabolic inhibitors for use in blood collection tubes, the volume of the anticoagulant potassium oxalate should be 20 μl and the volume of the metabolic inhibitor sodium fluoride is 12 μl.

The beads of the invention can be made in a wide range of sizes, depending upon the volume of solution used to prepare them. Typically, the beads will have a diameter of less than about 10 mm, usually less than about 5, or in some applications about 3.5 mm. The minimum size is typically about 1.5 mm.

The beads dissolve quickly in a sample solution. In the analysis of a biological sample, the sample will typically be in an aqueous solution. Sample solutions in other applications may include nonaqueous solutions. For instance, in food chemistry, methanolic solutions are used. The beads typically dissolve in less than about 30 seconds, preferably less than about 10 seconds, more preferably in less than about 1 second and in some cases less than about 0.3 seconds. In some case, the rapidity of dissolution gives the impression that the bead "explodes" and distributes the dissolving chemicals throughout the reconstituting volume. In other cases, the chemicals dissolve so rapidly that they are concentrated into the first fluid contacting the bead. Rapid dissolution of the beads is facilitated by a chemical lattice structure which quickly conducts water into the bead. To form the chemical lattice, fillers are included in the aqueous solution used to produce the beads. As the beads are lyophilized, these molecules facilitate formation of a network of open spaces or a chemical lattice in the beads. The filler components of the beads are typically polymeric compounds, such as bovine serum albumin, polyethylene glycol, dextran, Ficoll® (Pharmacia LKB Biotechnology, Inc., Piscataway, N.J.), or polyvinylpyrrolidone. In addition, emulsifiers such as sodium cholate and the like are useful as fillers. Monosaccharides and their derivatives, such as mannitol or the polyalcohol, myo-inositol, can also be used. Depending upon the particular application, the fillers can be used individually or in combination with one or more of the other filler components. In some cases, such as sodium fluoride and potassium oxalate, no filler is needed.

In addition to fillers, the beads of the present invention also comprise surfactants at concentrations sufficient to inhibit bubble formation when the beads are rapidly rehydrated. As described above, bubbles are detrimental to the assays because they interfere with optical measurements. If the beads comprise surfactants at the appropriate concentrations, however, such problems are avoided. Suitable surfactants include non-ionic detergents such as polyoxyethylene 9 lauryl ether, octoxynol 9, Synthrapol®, NP-90, Trycol® 5941, Trycols 6735 and the like. Ionic detergents such as Gafac® 560, sodium dodecyl sulfate and the like are also suitable. Typically, the surfactants are present in the reconstituted beads at a concentration between about 0.08 g and about 31 g per 100 ml. The surfactant concentration used will depend upon the particular reagent used in the assay.

The fillers and surfactants used in a particular dried bead preparation are preferably selected so as to minimize interference with the assay or other application. Optimization of the these components is facilitated by Table 1 which provides information regarding desired characteristics of fillers and surfactants suitable for use with reagents used in a variety of assays. In addition, the Example section below provides the precise concentrations of filler and surfactant components which have been found to be particularly useful in the exemplified assays.

In order to provide beads of the correct size in a test well, the components are typically concentrated in the bead. Upon rehydration with a predetermined volume of sample, the reagents and other components are present in the correct concentration. For instance, the components of the reagent beads for alkaline phosphate determinations are typically at about 6× concentration and total protein reagents are at about 2.7× concentration. In the case of sodium fluoride, it can be dispensed as a slurry of 12% (w/v). The ideal concentration for the reagents for particular assay can be easily determined, depending upon desired size of the bead, sample volume, and the like.

TABLE 1

(g/100 ml)

| | fillers | | | | | | | | surfactants | | | | | |
|---|---|---|---|---|---|---|---|---|---|---|---|---|---|---|
| | PEG 3400 | PEG 8000 | PEG 20M | Dextran | bovine albumin | PVP | inositol | mannitol | Mega 8 | n-Octyl glucoside | Triton X-100 | Trycol | Thesit | cholic acid |
| ALP A | | 5.40 | | | | 0.10 | 1.0 | | | | 0.08 | | | |
| ALP B | | 5.40 | | | | 0.10 | 1.0 | | | | 0.08 | | | |
| Amylase | | 4.00 | | | | | 2.0 | | | | 0.30 | | | |
| AST | | 2.50 | | 2.50 | 2.50 | | | | | | 0.40 | | | |
| BUN | | 4.00 | | | | | | | | | 0.30 | | | |
| Cholesterol (BMD) | | 0.87 | | | 3.70 | | | | | | | | | |
| CRP | | 8.40 | | | | | | | | | 0.30 | | | |
| Creatinine Test | | | | | | | | | | | 0.21 | | | 2.0 |
| Creatintine Blank | | | | | | | | | | | 0.25 | | | 2.0 |
| Glucose | | 1.80 | | | 2.10 | | | | | | 0.30 | | | |
| Plasma Dilution | 6.0 | | 1.00 | | 2.00 | | 1.0 | | | | 0.38 | 2.10 | | 10.0 |
| Rotor Q.C.A | 8.0 | | 3.00 | | | | | | | | 0.50 | | | |
| Rotor Q.C.B | 5.0 | | 2.00 | | | | 1.0 | | | | 0.50 | | | |
| Sample Blanking | | 9.60 | | | | | | | | | 0.80 | | | |
| Temperature | | | | 1.00 | | 0.10 | | 10.00 | 0.20 | 0.20 | | | | |
| Bilirubin Enzyme | | | | 2.00 | | | 1.0 | 6.00 | | | | | | |
| Bilirubin Buffer | | 8.00 | | | | | | | | | | | | |
| Total Protein | 5.00 | 4.00 | 0.50 | | | | | | | | | | 0.143 | 0.5 |

TABLE 1-continued (g/100 ml)

| | fillers | | | | | | | surfactants | | | | | |
|---|---|---|---|---|---|---|---|---|---|---|---|---|---|
| | PEG 3400 | PEG 8000 | PEG 20M | Dextran | bovine albumin | PVP | inositol | mannitol | Mega 8 | n-Octyl glucoside | Triton X-100 | Trycol | Thesit | cholic acid |
| Triglycerides Blank | | 1.80 | | 3.60 | 3.60 | | | | | | 0.15 | 0.30 | | 0.1 |
| Triglycerides Test | | 1.80 | | 3.60 | 3.60 | | | | | | 0.15 | 0.30 | | 0.1 |
| Uric Acid | | 4.00 | | | | | | | | | 0.24 | | | |

The following examples show preparation of reagent beads for particular assays. These examples are provided by way of illustration and not by way of limitation.

EXAMPLE 1
Preparation of Reagent Beads for Total Protein Determination

The following solution was prepared by accurately weighing and dissolving the following chemicals in a container of about 800 ml of deionized or distilled water:

| | |
|---|---|
| sodium potassium tartrate | 37.80 g |
| sodium hydroxide pellets | 28.20 g |
| cupric sulfate | 12.00 g |
| potassium iodide | 12.90 g |
| sodium carbonate | 3.85 g |
| sodium cholate | 5.00 g |
| polyoxyethylene 9 lauryl ether | 1.43 g |
| polyethylene glycol (FW 3400) | 50.00 g |
| polyethylene glycol (FW 8000) | 40.00 g |
| polyethylene glycol (FW 20,000) | 5.00 g |

It is best to completely dissolve each chemical before adding the next chemical. After the last chemical dissolved, the solution volume was adjusted to 1.0 liter with deionized or distilled water. The solution was filtered through a stack of media that terminated in 0.45 micron porosity. The solution was then degassed using a vacuum pump. The above solution when diluted 37 ml plus 63 ml with water is used to assay Total protein concentration in various clinical samples such as serum or plasma. The sodium carbonate is added as a stabilizer, and polyoxyethylene 9 lauryl ether is added for controlling bubbles during dissolution. Sodium cholate and the various polyethylene glycols are added as fillers to facilitate formation of a chemical lattice during subsequent freeze drying.

The solution was dispensed by an IVEK model AAA pump in discrete 2.96 microliter drops at a rate of 1 to 2 drops-per-second. The discrete amounts of fluid drop through air, form beads and land on the surface of liquid nitrogen. The surface of the nitrogen does not need to be agitated. After freezing the beads were dried in Virtis freeze dryer (model no. 12EL console) (Gardener, N.Y.) until their residual moisture were less than 11% of the total remaining mass.

A freeze dried reagent bead prepared according to the above method can be reconstituted with 8 microliters of a mixture of water or diluent (14 parts) and human serum (1 part). The resulting change in absorbance at 550 nm minus the absorbance of a reagent bead reconstituted with 8 microliters of water or diluent and minus the absorbance of the human serum sample diluted in the same ratio with water plus polyoxyethylene 9 lauryl ether and sodium cholate is proportional to the amount of total protein in the sample.

The imprecision (coefficient of variation) among the 1.78 millimeter diameter beads is:

| | |
|---|---|
| dispensed frozen beads | 1.5% at 3.7 mg |
| freeze dried beads | 2.5% at 0.6 mg |

Each reagent bead dissolves in 8 microliters of water or diluent within 5 seconds in a centrifugal analyzer.

EXAMPLE 2
Preparation of Reagent Beads for C-Reactive Protein Determination

The following solution was prepared by accurately measuring weighing and dissolving the following chemicals in a container of about 200 mls of deionized or distilled water:

| | |
|---|---|
| C-reactive protein antibody | 0.56 liters |
| Sodium chloride | 25.50 g |
| HEPES | 71.50 g |
| Triton ® X-100 | 3.00 g |
| polyethylene glycol (FW 20,000) | 84.00 g |

It is best to completely dissolve each chemical before adding the next chemical. After the last chemical dissolved, the pH was adjusted to 7.4 with dilute sodium hydroxide and the solution volume was adjusted to 1.0 liter with deionized or distilled water. The solution was filtered through a stack of media that terminated in 0.2 micron porosity. The solution was then degassed.

The above solution when diluted 33 ml plus 67 ml with water or diluent is used to assay C-reactive protein in various clinical samples such as serum or plasma. The sodium chloride is added as a stabilizer and Triton® X-100 is added for controlling bubbles during dissolution. Polyethylene glycol is added to facilitate the development of turbidity in the analytic reaction and as filler to facilitate formation of a chemical lattice during subsequent freeze drying.

The solution was dispensed by an IVEK model AAA pump in discrete 2.67 microliter drops at a rate of 1 to 2 drops-per-second. The discrete amounts of fluid drop through air, form beads and land on the surface of liquid nitrogen. The surface of the nitrogen does not need to be agitated. After freezing, the beads were dried in a Virtis freeze dryer (model no. 12EL console) until their residual moisture were less than 6% of the total remaining mass.

A freeze dried reagent bead prepared according to the above method can be reconstituted with 8 microliters of a mixture of water or diluent (14 parts) and human serum (1 part). The resulting change in absorbance at 340 nm minus the absorbance of a reagent bead reconstituted with 8 microliters of water or diluent and minus the absorbance of the human serum sample diluted in the same ratio with water plus Triton® X 100 is proportional to the amount of C-reactive protein in the sample.

The imprecision (coefficient of variation) among the 1.72 millimeter diameter beads is:

| dispensed frozen beads | 1.7% at 2.9 mg |
|---|---|
| freeze dried beads | 1.8% at 0.5 mg |

Each reagent bead dissolves in 8 microliters of water or diluent within 3 seconds in a centrifugal analyzer.

EXAMPLE 3
Preparation of Reagent Beads for Alkaline Phosphatase (ALP) Determination The following solutions were prepared. ALP part A: The following chemicals were accurately measured, weighed, and dissolved in a container of about 800 mls of deionized or distilled water:

| Tris (hydroxymethyl) aminomethane-HCL | 10.2 g |
|---|---|
| HEDTA | 2.1 g |
| magnesium chloride hexahydrate | 2.6 g |
| zinc sulfate heptahydrate | 1.7 g |
| 4-nitrophenylphosphate | 35.6 g |
| polyethylene glycol (FW 20,000) | 54.0 g |
| myo-inositol | 10.0 g |
| Triton ® X-100 | 0.8 g |
| glycerol | 6.0 g |
| polyvinylpyrrolidone (FW 30,000) | 1.0 g |

It is best to completely dissolve each chemical before adding the next chemical. After the last chemical dissolved, the pH was adjusted to 6.8 with dilute 2-amino-2-methyl-1-propanol and the solution volume was adjusted to 1.0 liter with deionized or distilled water. The solution was filtered through a stack of media that terminated in 0.2 micron porosity. The solution was then degassed.

ALP part B: The following chemicals were accurately measured, weighed, and dissolved in a container of about 800 mls of deionized or distilled water:

| Tris (hydroxymethyl) aminomethane-HCL | 10.2 g |
|---|---|
| Tris (hydroxymethyl) aminomethane | 166.0 g |
| HEDTA | 2.1 g |
| polyethylene glycol (FW 20,000) | 54.0 g |
| myo-inositol | 10.0 g |
| Triton ® X-100 | 0.8 g |
| 2-amino-2-methyl-1-propanol | 53.4 g |
| polyvinylpyrrolidone (FW 30,000) | 1.0 g |

It is best to completely dissolve each chemical before adding the next chemical. After the last chemical dissolved, the pH was adjusted to 10.3 with dilute 2-amino-2-methyl-1-propanol and the solution volume was brought to 1.0 liter with deionized or distilled water. The solution was filtered through a stack of media that terminated in 0.2 micron porosity. The solution was then degassed.

The above solutions when combined in equal volumes of 16.7 ml each and 67 ml of water or diluent are used to assay alkaline phosphatase in various clinical samples such as serum or plasma. The glycerol is added as a stabilizer. Triton® X-100 is added for controlling bubbles during dissolution. Polyethylene glycol, myo-inositol, and polyvinylpyrrolidone are added as fillers to facilitate formation of a chemical lattice during subsequent freeze drying.

The solutions were dispensed separately by an IVEK model AAA pump in discrete 2.67 microliter drops at a rate of 1 to 2 drops-per-second. The discrete amounts of fluid drop through air, form beads and land on the surface of liquid nitrogen. The surface of the nitrogen does not need to be agitated. After freezing the beads were dried in a Virtis freeze dryer (model no. 12EL console) until their residual moisture were less than 6% of the total remaining mass.

One of each, ALP A and ALP B, freeze dried reagent beads can be reconstituted with 16 microliters of a mixture of water or diluent (14 parts) and human serum (1 part). The resulting rate of change in absorbance at 405 nm is proportional to the amount of alkaline phosphatase in the sample.

The imprecision (coefficient of variation) among the 1.72 millimeter diameter beads is:

|  | ALP A | ALP B |
|---|---|---|
| dispensed frozen beads | 0.4% at 2.8 mg | 0.7% at 2.9 mg |
| freeze dried beads | 1.5% at 0.5 mg | 2.2% at 0.7 mg |

The two reagent beads dissolve in 16 microliters of water or diluent within 10 seconds in a centrifugal analyzer. The active constituents in this assay are separated to improve reagent stability. One of each of the beads is placed in the same chamber for the ALP assay.

EXAMPLE 4
Preparation of Freeze-Dried Concentrated Potassium Reagent Containing Macrocyclic Ionophore Trinitroanilino Cryptahemispherand [2.2] for Potassium Determination The active trinitroanilino cryptahemispherand [2.2] and surfactants (Brij® surfactants) were isolated from ChromoLytew Potassium Reagent (Technicon Instruments Corp., Tarrytown, N.Y. 10961) using Wide-Pore Butyl, 40 μM chromatographic medium (J. T. Baker Inc., Phillipsburg, N.Y. 08865) as follows:

25 g of Wide-Pore Butyl, 40 μM chromatographic medium were suspended in 360 ml of degassed isopropanol and then 360 ml of degassed deionized water was added. About 80% of the liquid was decanted. An additional 360 ml portion of degassed deionized water was added and the slurry in the flask was sonicated for two minutes, followed by two minutes of vacuum degassing. The suspended chromatographic medium was poured into an appropriately sized chromatographic column to form a 3–10 cm high packing bed. The packing was equilibrated by passing 250 ml of degassed deionized water through the column.

Five liters of ChromoLyte™ Potassium Reagent were applied to the column. The colored trinitroanilino cryptahemispherand [2.2] and the surfactants were adsorbed on the top of the column. The nonadsorbed triethanolamine buffer, also containing 3% of 2-(2-ethoxyethoxy)-ethanol (EEE) and stabilizers, was collected and saved for later use. The trinitroanilino cryptahemispherand [2.2] and the surfactants were eluted from the column with a mixture of previously degassed isopropanol (98%) and EEE (2%). The isopropanol was removed from the eluate using an evacuated rotary evaporator at room temperature to yield an oily, dark brown concentrate.

The previously collected buffer fraction was concentrated twofold using an evacuated rotary evaporator at 35°–40° C. The concentrated trinitroanilino cryptahemispherand [2.2], the surfactants and the remaining EEE were dissolved in 400 ml of the twofold concentrated buffer solution.

The following materials were measured, added and dissolved in the above solution:

| polyethylene glycol (FW 3400) | 40 g |
| isopropanol | 5.0 ml |
| polyvinylpyrrolidone K-29-32 | 0.50 g |

The pH of the solution was measured using an electrode pair with a calomel reference electrode to verify that the pH was less than 0.05 pH unit different from the pH of the starting ChromoLyte™ Potassium Reagent. If necessary, pH adjustment was made with a 20% triethanolamine solution or with a 20% triethanolamine HCl solution. Finally, the volume was adjusted to 500 ml with the twofold concentrated buffer solution. The reagent was filtered through a stock of media that terminated in 0.2 micron porosity. The preferred concentration of 2-(2-ethoxyethoxy)-ethanol is between about 3% and about 4.8%, and that of the polyethoxylauryl ether is between about 0.5 and about 1.0%.

The above solution when diluted 50 ml plus 50 ml with water or diluent is used to assay potassium in various clinical samples such as serum or plasma. The level of 2-(2-ethoxyethoxy)-ethanol is necessary to insure uniform freezing of the reagent and to aid in rapid resolubilization after freeze-drying. The isopropanol aids in creating the correct crystal structure during the freezing process so that the rehydration is facilitated. The Brij® surfactant (e.g., Brij® -35 or -58) aids in rehydration and in bubble inhibition. The polyethylene glycol is added to facilitate formation of a chemical lattice during subsequent freeze drying.

The solution was dispensed by an IVEK model AAA pump in discrete 4.0 microliter drops at a rate of 1 to 1.5 drops-per-second. The discrete amounts of fluid drop through air, form beads were dried in a Virtis freezer dryer (model no. 12 EL console) until their residual moisture were less than 6% of the total remaining mass. A freeze dried reagent bead prepared according to the above method can be reconstituted with 8 microliters of a mixture of water or diluent (14 parts) and human serum (1 part). The resulting change in absorbance at 500 nm minus the absorbance of a reagent bead reconstituted with 8 microliters of water or diluent and minus the absorbance of the human serum sample diluted in the same ratio with water plus Brij® surfactant is proportional to the amount of potassium in the sample.

The imprecision (coefficient of variation) among the 1.97 millimeter diameter beads is:

| dispensed frozen beads | 1.5% at 2.6 mg |
| freeze dried beads | 1.6% at 0.5 mg |

Each reagent bead dissolves in 8 microliters of water or diluent within 5 seconds.

EXAMPLE 5
Preparation of Sodium Fluoride Beads

The following solution was prepared. To a volumetric flask containing 85 ml of deionized water was added 12.0 g of sodium fluoride. The volume was than adjusted to 100.0 ml with additional deionized water. The solution was vigorously mixed until a uniform slurry was formed. The slurry was continuously mixed during dispensing by an IVEK model AAA pump in 6.0 ul drops at a rate of 1 or 2 drops per second. The discrete amounts of fluid drop through air, form beads and land on the surface of liquid nitrogen. After freezing the beads were dried in a Virtis freeze dryer (model no. 12EL console). Seven beads of sodium fluoride are required to arrest glycolysis per 2 ml of blood.

The Imprecision (coefficient of variation) among the 2.25 millimeter diameter beads is:

| dispensed frozen beads | 0.6% at 3.0 mg |
| freeze-dried beads | 2% at 0.5 mg |

Seven beads dissolve in 2.0 ml of blood within 10 seconds, with a single inversion of the container to mix the sodium fluoride with the blood.

EXAMPLE 6
Preparation of Potassium Oxalate Beads

The following solution was prepared. To a volumetric flask containing 75 ml of deionized water was added 20.0 g of potassium oxalate. The volume was then adjusted to 100.0 ml with additional deionized water. The solution was vigorously mixed until dissolved. The solution was continuously mixed during dispensing by an IVEK model AAA pump in 20.0 ul drops at a rate of 1 to 2 drops per second. The discrete amounts of fluid drop through air, form beads and land on the surface of liquid nitrogen. After freezing the beads were dried in a Virtis freeze dryer (model no. 12EL console). One bead of potassium oxalate is required to prevent coagulation per 2 ml of blood.

The Imprecision (coefficient of variation) among the 3.37 millimeter diameter beads is:

| dispensed frozen beads | 0.4% at 21 mg |
| freeze-dried beads | 0.7% at 2.5 mg |

One bead dissolves in 2.0 ml of blood within 10 seconds, with a single inversion of the container to mix the potassium oxalate with the blood.

The above examples illustrate preparation of particular reagent beads within the scope of the present invention. The examples have been provided for the purposes of clarity and understanding the invention. It will be apparent, however, that certain changes and modifications may be practiced within the scope of the appended claims.

What is claimed is:

1. A container holding a dried chemical composition which dissolves in less than about 10 seconds in water, wherein said dried chemical composition comprises a preselected precisely measured aliquot of said dried chemical composition which chemical composition is in bead form have in a diameter between 1.5 mm and 10.0 mm.

2. The container of claim 1, which is a cuvette in a centrifugal rotor.

3. The container of claim 1, wherein the dried chemical composition has a diameter between about 1.5 mm and 3.5 mm.

4. The container of claim 1, wherein said dried chemical composition is produced by a method comprising the steps of:

forming a solution comprising a desired compound;

dispensing uniform, precisely measured drops of the solution into a cryogenic liquid, whereby the drops are frozen; and drying the frozen drops, thereby forming dried aliquots wherein the dried aliquots comprise a plurality of dried aliquots having a coefficient of weight variation of less than about 3 % and wherein said dried chemical composition is a single aliquot selected from the plurality of dried aliquots.

* * * * *